United States Patent [19]
Thomsen et al.

[11] Patent Number: 5,981,605
[45] Date of Patent: Nov. 9, 1999

[54] GEL FOR TREATMENT OF SKIN DISEASES AND FOR DISINFECTION OF THE SKIN

[75] Inventors: John Brown Thomsen, "La Campagne", 587 chemin du Clot, F-06510 Gattières, France; Jens Christian Møller, Lemvig, Denmark

[73] Assignee: John Brown Thomsen, Gattieres, France

[21] Appl. No.: 08/714,162

[22] PCT Filed: Mar. 20, 1995

[86] PCT No.: PCT/EP95/01025

§ 371 Date: Oct. 29, 1996

§ 102(e) Date: Oct. 29, 1996

[87] PCT Pub. No.: WO95/25544

PCT Pub. Date: Sep. 28, 1995

[30] Foreign Application Priority Data

Mar. 21, 1994 [DK] Denmark .................................. 0325/94

[51] Int. Cl.⁶ .......................... A61K 47/10; A61K 47/38; A61K 9/70
[52] U.S. Cl. .................. 514/724; 514/772.1; 514/772.5; 514/772.6; 514/781; 514/969; 514/970; 514/777
[58] Field of Search .............................. 514/724, 772.1, 514/772.3, 772.5, 772.6, 777, 781, 969, 970

[56] References Cited

U.S. PATENT DOCUMENTS

| | | | |
|---|---|---|---|
| 3,016,328 | 1/1962 | Pepper et al. | 167/22 |
| 4,247,547 | 1/1981 | Marks | 424/240 |
| 4,590,214 | 5/1986 | Zamore | 514/702 |
| 4,593,048 | 6/1986 | Sato et al. | 514/778 |
| 4,671,955 | 6/1987 | Palinczar | 424/47 |
| 4,849,455 | 7/1989 | Eggers | 514/724 |
| 4,992,475 | 2/1991 | Marcel | 514/718 |
| 5,013,545 | 5/1991 | Blackman et al. | 424/81 |
| 5,098,717 | 3/1992 | Blackman | 514/648 |
| 5,145,663 | 9/1992 | Simmons | 424/47 |
| 5,288,486 | 2/1994 | White | 424/78.08 |
| 5,331,012 | 7/1994 | Riddick et al. | 514/626 |

FOREIGN PATENT DOCUMENTS

| | | |
|---|---|---|
| 0 176 720 | 4/1986 | European Pat. Off. . |
| 0 320 254 | 6/1989 | European Pat. Off. . |
| 466 134 | 1/1992 | Sweden . |
| 2 017 491 | 10/1979 | United Kingdom . |
| 1 593 097 | 7/1981 | United Kingdom . |
| 93/00114 | 1/1993 | WIPO . |

OTHER PUBLICATIONS

Seelig and Gould, "Osmosis As an Important Factor in the Action of Antiseptics", manuscript presented to Western Surgical Association Dec. 10, 1910, pp.262–270.

Harrington, "The Germicidal Action of Alcohol", *Boston Medical and Surgical Journal* (1903) pp. 548–552.

Christiansen, "Zur Theorie und Praxis der Alkoholdesinfektion", *Aus dem Institut fur allgemeine Pathologie in Kopenhagen* (1918) pp.275–305.

H.E. Morton, "Alcohols" in Disinfection, Sterilization and Preservation, $2^{nd}$ Ed., pp. 301–318, 1997.

J.B. Thomsen, "Concentration/Formulation Experiments" —Declaration, Aug., 1998.

S. Mogensen, Blackman et al. —Declaration, Sep., 1998.

H. K. Andersen, In Vitro Antiviral—Declaration, Sep., 1998.

F.T. Black, Clinical Trial—Declaration, Sep., 1998.

Microbiology: An Introduction, Fifth Edition, Tortora, Funke and Case, Benjamin Cummings Publishing Co., 1994.

"A Surface Test for Virucidal Activity of Disinfectants: Preliminary Study with Herpes Virus", R. Tyler et al, Journal of Hospital Infection (1987) 9, 22–29.

"Quantitative Evaluation of the Effects of Disinfectants Against Viruses in Suspension Experiments", D. Moldenhauer, pp. 544–554 (1984).

"In Vitro Virucidal Activity by Components of a Topical Film–Forming Medication", B. Rodu et al, J. Oral Pathol 1988, 17:324–326.

Chem. Abstract, 90:76562r (1979).

*Primary Examiner*—Frederick Krass
*Attorney, Agent, or Firm*—Burns, Doane, Swecker & Mathis, L.L.P.

[57] ABSTRACT

Gel for local treatment of skin diseases and for prophylaxis, characterised by containing more than 90% of a drying and/or protein coagulating, short-chained alcohol or alcohol mixture, primarily ethanol, and possibly adjuvants or additives and by containing a gelling agent, that possesses good skin-adhesive properties, that gives a matrix formation of alcohol or alcohol mixtures, that creates an evaporation-inhibiting effect, gives a prolonged effect, and forms a protective plaster when the gel has dried.

32 Claims, No Drawings

GEL FOR TREATMENT OF SKIN DISEASES AND FOR DISINFECTION OF THE SKIN

This application concerns a matrix-forming and skin-adhesive, anti-evaporant gel for local treatment of skin diseases, for both primary and secondary prophylactic treatment of wounds, and for skin disinfection or the like in both humans and animals. More precisely, the invention relates to a gel characterized by containing lower alkanol in a concentration of more than 90% and by containing a gelling agent, such as ethyl(hydroxyethyl)cellulose or another suitable gelling agent, and possible additives, whereby the gel can be applied to the skin efficiently, easily, and without complications.

BACKGROUND

Infectious skin diseases, both microbial and parasitic, are widespread. Some examples of skin diseases are viral skin infections caused by, for example, Herpes simplex virus or Varicellae Zoster virus, bacterial skin infections caused by, for example, *Staphylococcus aureus,* fungal infections caused by, for example, *Trichophyton rubrum,* for eliminating skin parasites, such as *Sarcoptes scabiei* var. hominis. The virus infection, Herpes simplex, alone occurs with approximately 100 million new cases per year.

Herpes simplex is caused by Herpes simplex virus (HSV). This virus occurs in two antigenically different types, type 1 and type 2. Herpes on the lips and around the mouth (*Herpes labialis*) is usually caused by type 1; most incidences of Herpes on and around the genitals (*Herpes genitalis*) are caused by type 2.

The first infection with HSV (primary infection) varies symptomatologically. Usually it occurs during childhood. At this first infection, HSV-DNA is incorporated into the cells. Intermittently, virus proliferation occurs, resulting in Herpes outbreaks from this incorporated HSV-DNA (these outbreaks are called secondary infections). Most Herpes outbreaks in adults are secondary, where the infection flares up due to reduced resistance, febrile diseases (e.g. Pneumonia), traumas, or the effects of cold, heat, or light.

The outbreak starts with flushing, swelling, itching, and pain in the infected area followed by necrosis and a suppurative ulceration which is the most troublesome symptom. A spontaneous healing of the wounds will occur in approximately 10 to 14 days.

The outbreak of *Herpes genitalis*—mentioned above—is identical to that of *Herpes labialis* except for the fact that *Herpes genitalis* is located on and around the genitals.

The number of therapeutics for, for example, HSV skin infections is very limited, and the present antiviral chemotherapy has not convincingly been proved efficient. Furthermore, there exists a few products for advancing the healing of established HSV-wounds and inhibition of further outbreaks. However, none of these products have a convincing effect.

Bacterial infections such as pimples, isolated or in connection with Acne vulgaris, are examples of other skin diseases for which adequate treatments are not currently available. In Acne it is currently believed that lipolysis of triglycerides by *Propionibacterium acnes* releases fatty acids; it is thought that these fatty acids are capable of eliciting an inflammatory process in the follicle wall, which may then rupture. Discharge of the follicular content leads to perifollicular inflammation. Benzoyl peroxide, which is currently used for-treating acne, has a mode of action dependent upon its broad-spectrum antimicrobial effect on both primary inflammation and on secondary infection. Current treatments based on benzoyl peroxide have inherent problems, including lack of efficacy and adverse reactions such as erythema, burning and desquamation of the skin.

From the literature it is known to use alcohol as disinfectant against, for example, virus including HSV—see, for example, R. Tyler; Journal of Hospital Infection (8: 22–29; 1987). When using alcohols as normal liquids a poor and very brief effect is achieved due to the very rapid evaporation of the alcohols. Also the use of alcohols at concentrations below 90% by weight gives inadequate results.

Furthermore, Moldenhauer, in Zbl. Bakr. Hyg., I Abt. Orig. B 179, 544–554 (1984) compares surface disinfection properties of ethanol, isopropanol, formaldehyde and benzalkonium chloride by suspending virus suspension (including HSV, influenza, cocksackie-B and mumps) in those compounds or solutions. Alcohol concentrations above 90% were not tested. Furthermore in these two references alcohol is being used for surface disinfection properties and not for treatment of infections and the symptoms thereof.

In U.S. Pat. No. 5,145,663, a disinfectant, consisting of 65–75% isopropyl alcohol, 8–12% propylene glycol, and potential inert ingredients or disinfectants or antiseptics, is mentioned. The patent does not mention gels.

In GB-A-2017491 a gel containing alcohol is used as a hand-wash for bacterial disinfection.

In the above references describing the use of alcohol, either as such or as a solvent for other active disinfectant agents, in surface disinfection of the skin, the alcohol will remain in contact with the skin for a relatively short period of time. The compositions, if they are washing compositions when they may contain a thickener such as sodium chloride, are generally rinsed off with water. Treatment with no-rinse compositions and alcohol wipes applies a relatively low amount of composition and the alcohol evaporates quickly. The alcohol is, in particular, not in contact with the skin long enough for penetration to layers below the stratum corneum (dermis and epidermis).

Ethanol has been used extensively in pharmaceutical compositions used for topical application to the skin. Compositions including a gelling agent have, likewise, been used for such application. However in none of these disclosures is the alcohol itself used as an agent for treating skin diseases. The following references are relevant.

In U.S. Pat. No. 3,016,328 and in U.S. Pat. No. 4,590,214 a mixture of a dialdehyde and an alcohol is mentioned. Without evaluating the effect, it can be established that none of these products include alcohol and gel-forming agents.

WO 93/00114 describes a method for reducing the duration of HSV-infection by applying a mixture of an anaesthetic and a surface-active ingredient with suitable antiviral activity. It does not mention gelling agents.

U.S. Pat. No. 4,247,547 mentions the use of gels containing alcohols and the dermatologically active tretinoin for treatment of acne. Tretinoin is an irritant and the compositions would be wholly unsuitable for treatment of skin infected by HSV. Also the concentration of water in the compositions is unclear.

In Chemical Abstracts 90:76564r (1979) an antiseptic paste is disclosed containing about 80% by weight ethanol, 13% water and a thickener.

U.S. Pat. No. 5,013,545 describes a gel consisting of 60–90% ethanol, 0.5–30% water, and an active ingredient, such as an antihistamine. This patent does not mention activity on viral skin infections such as Herpes. Further, none of the worked examples teaches how to produce a stable gel with more than 80% alcohol.

U.S. Pat. No. 5,098,717 describes a gel based on 60–90% ethanol and as active ingredients an antihistamine and an antipruritic.

Carrier gels for pharmaceuticals based on ethanol and water are described in the patent literature, see, for example, SE 466134. In U.S. Pat. No. 4,593,048 it is mentioned that the penetration into the circulation by pharmaceuticals, dissolved in ethanol and applied topically, is accelerated when various adjuvants are used. The formulation contains surface-active ingredients as penetration aids for pharmaceuticals for percutaneous systematic administration. The compositions are not used to treat skin disorders.

An article by B. Rodu and F. Lakeman ("In vitro virucidal activity by component of a topical film-forming medication," J. Oral Pathology 17: 324326; 1988) mentions in vitro trials of a preparation consisting of approximately 80% ethanol, 7% tannic acid, 2.5% salicylic acid, and 1% boron acid. The tests were intended to evaluate the in vitro properties of the product Zilactin, which contains those ingredients and a hydroxy propylcellulose gelling agent. The in vivo performance of the gel against HSV has, however been found to be limited.

A specific antiviral preparation for topical treatment of Herpes is Zovir/Zovirax cream (Zovir is a registered trademark), which contains 5% aciclovir. The efficacy has not been convincingly proved in relation to Herpes simplex skin infections, and, moreover, reports that resistance is beginning to develop have been published.

Acyclovir has been administered systemically for the treatment of Varicellae Zoster virus. However reports have indicated that the treatment limited the immune response with consequent failure to develop resistance to the disease.

Surprisingly, it has now turned out that it is possible to produce an effective gel for treating skin diseases and for controlling skin parasites without using anti-histamines, anaesthetics, anti-inflammatory agents, and totally without using pharmaceuticals, including biocides against skin parasites.

Ethyl hydroxy ethylcellulose (EHEC) is produced by a first swelling native cellulose in alkali, then adding ethylene oxide to cellulose hydroxyl groups activated in the first step, then etherifying hydroxyl groups in the product by reacting them with ethyl chloride after alkali treatment. In the ethylene oxide treatment step ethoxy units may be added to the hydroxyl group on a pendant group derived from the earlier reaction of an ethylene oxide molecule with a cellulose-hydroxyl group. In the etherification step, hydroxyl groups of pendant groups and of cellulose-hydroxyl group may be reacted. The polymer product thus contains ethoxy 2-ethoxyethyleneoxy and ethoxypoly(ethyleneoxy) pendant groups. The reactions can be controlled so as to provide EHEC products with a variety of different degrees of substitution, and molar substitution (i.e. a measure of the average ethyleneoxy units per etherified group). These parameters, as well as the degree of polymerisation/ molecular weight, affect the properties of the polymer in solution.

The performance of EHEC in aqueous systems, where it is used as a thickener and dispersing agent, for instance in paints and cement based mortar, has been studied (Tornquist, J, Farg och Lack Scandinavia, 31, 291–295 (1985), Carlsson, A et al polymer, 27, 431–436 (1986)). We are not aware that its use to thicken or gel non-aqueous alcohols has been studied.

SUMMARY OF THE INVENTION

A new gel-form pharmaceutical composition according to the invention comprises a liquid and a high molecular weight polymer gelling agent dissolved in the liquid, characterised in that the composition comprises more than 90% by weight of a lower alkanol based on the total weight of the composition and less than 10% by weight water based on the total weight of the composition.

The composition optionally comprises one (or more) enhancing agent which enhances the effect of the alcohol. Preferably the composition is substantially free of antihistamines, anaesthetics, anti-inflammatories, irritants and any immunogenic compounds or compounds which disturb the immune system. Consequently, in the invention, concentration and crystallization of medicaments (which is a potential problem with prior art compositions in which alcohol is held as a solvent vehicle for such active compounds) will not occur when the solvent evaporates. Consequently, local overdosing resulting in irritative inconveniences is totally avoided.

The lower alkanol preferably contains up to 4, preferably up to 3 carbon atoms. It may be a glycol or polyol but is preferably a mono hydroxy compound. It can be a mixture of such compounds. Most preferably it includes ethanol optionally in combination with other lower alkanols.

Thus, it has now surprisingly been found that a gel containing more than 90% ethanol or other lower alkanol is very effective for local treatment of, for example, skin infections and skin parasites.

When using suitable gelling agents it is possible to transform a concentrated alcohol into a very suitable, effective, and stable gel. The invention is of particular value in the treatment of viral infections whose systems involve skin eruptions, especially herpes infections.

DETAILED DESCRIPTION OF THE INVENTION

Thus, the preparation of the invention consists of concentrated alcohol in such a form that it is usable as a topical preparation for immediate application to the infected area of the skin including mucous membranes. While ethanol in lower concentrations, for example in concentrations of less than 60%, gives a distinct pain reaction, the use of the concentrated alcohol, for example in concentrations of more than 90% according to the invention, is almost painless even when it is used in open wounds. The preparation has a combined effect which is utilised optimally and over a prolonged period in the invention. Thus, an effective combination of drying the edematous tissue, coagulating proteins and killing the infectious agent, is achieved, and later, when it has dried, the gelling agent acts as a plaster protecting against infection.

The gels of the invention create a matrix formation that prevents the alcohol from leaking out of the gel and flowing away from the site where the gel has been applied. At the same time the gel is gentle to the skin and easy to apply. It is possible, and preferred, for the composition to be transparent, and for the dried film of polymer gelling agent, remaining after the composition has dried on the skin, to be transparent to allow the underlying skin to be visible throughout treatment.

When the gel has dried it forms a protective film over a wound such as an HSV outbreak. Separately, all these activities contribute to avoid secondary bacterial infection. With the evaporation-limiting matrix formation the gel forms a barrier film on the surface between gel and air by means of which the evaporation of alcohol is drastically reduced. For a long time the alcohol in this way remains in contact with the skin by which means the ethanol has a possibility of diffusing into the skin and perform its effect in depth. Further, the plaster action of the gel prevents a rapid evaporation of the alcohol diffused into the tissue and, finally, after drying the plaster effect of the gel will offer protection against reinfection of the affected area. Thus, when choosing a gelling agent or a mixture of gelling agents, which form matrix with the ethanol and that form a film on the surface of the gel against the atmosphere, the extraordinary prolonged effect of the gel is achieved according to the invention.

The content of water is important to the effectiveness. The content should be less than 10%, preferably less than 5%, and optimally, in some cases, less than 1%. The amount of water should be below the equilibrium content of the composition under ambient conditions, that is under normal storage conditions at 20–24° C. and at 50–100% relative humidity, as well as at such humidity levels at temperatures up to body temperature (eg 37° C.). Thus the composition as a whole should, in effect be hygroscopic. The hygroscopicity is preferably due to the concentration of alkanol being higher than the concentration of alkanol in the presence of humid air. The equilibrium concentration of water in ethanol under these conditions is in the range 3 to 7% by weight of the sum of water and ethanol. The gelling agent may also contribute some hygroscopicity. If the content of water is too high the drying and antimicrobial effect and especially the antiviral effect is reduced which means that the effectiveness of the gel is reduced. Similarly, the concentration of alkanol is crucial to the effect on external skin parasites. It seems that the high concentration of alkanol may allow the alkanol to penetrate to layers of skin below the stratum corneum.

One of or a combination of several gelling agents which are usually soluble in the alkanol can be used. The gelling agent is a polymer, which may be linear, branched or cross-linked and may be naturally-derived, a derivative of such polymers, or may be wholly synthetic. The molecular weight is usually high, for instance at least $10^4$, preferably at least $5 \times 10^5$, and up to several million, for instance more than $10^6$. The polymer is preferably non-ionic in the composition. Suitable gelling agents include cellulose derivatives, especially cellulose ethers, such as ethylcellulose, methylcellulose; hydroxyethyl cellulose especially ethyl(hydroxyethyl)cellulose (EHEC), alkyl- and hydroxyalkyl cellulose, carboxy methyl cellulose, other polysaccharides, such as naturally derived polysaccharides and derivatives thereof, including modified carragenan; and synthetic polymers such as polyethylene glycols, polyethylene oxides, polyvinyl pyrrolidones and poly acrylic acid.

The cellulose derivatives which are useful in the invention usually have a high molecular weight, for instance more than $10^6$, although polymers with molecular weight from $10^5$ upwards may be useful. The degree of substitution/derivatisation of cellulose ether derivatives useful in the invention is preferably relatively high, for instance higher than 1.0.

A particularly suitable cellulosic gelling agent for a highly concentrated ethanol is EHEC, ethyl(hydroxyethyl) cellulose, which is a derivative of cellulose with CA registration number 9004-58-4. EHEC is, as an example, sold under the trademark BERMOCOLL from Berol Kemi AB, such as BERMOCOLL OS. For example, an effectively gelling EHEC is achieved at degree of polymerisation of approximately 3,200, a degree of substitution of approximately 1.7 for ethylene (DS-ethyl=1.7) and of approximately 1.5 for hydroxyethyl (MS-hydroxyethyl=1.5). Celluloseethers including EHEC are more precisely described in Kirk-Othmer, "Encyclopedia of Chemical Technology," 5:143,1979(3. edition). See also "Faerg och Lack Scandinavia" 31:291–298;1985.

Acrylic acid polymerics are also particularly suitable as gelling agent. Acrylic acid polymerics are, as an example, sold under the trademark Carbopol from BF Goodrich, such as Carbopol 940 and 941, Carbopol 940 NF and 941 NF, Carbopol 980 NF and 981 NF, or Carbopol 1342 and 1382. Those Carbopols are high molecular, non-linear polymerics of acrylic acid cross-linked with polyalkenyl polyether. Acrylic acid polymerics are more precisely described in "Kirk-Othmer, Encyclopedia of Chem.Tech," 20:216;1982 and in Ullmanns Encyclopedia of Ind.Chem.," A21:752;1992.

Polyvinylpyrrolidones are a third example of a particularly suitable gelling agent. Polyvinylpyrrolidones, as an example, are sold under the trademark PVP K-30 and PVP K-90 from GAF. Polyvinylpyrrolidones are high molecular polymerics which are described in more detail in "Kirk-Otmer, Encyclopedia of Chem.Tech.," 23:963;1983 and in "Ullmanns Encyclopedia of Ind.Chem.," A21:143;1992 and others.

The gelling agents are used in amounts between 0.1% and 10%, depending on the choice of gelling agent or mixture of gelling agents, depending on the composition, the desired texture etc. The amount should preferably be sufficient to render the composition gel-like at room temperature and at normal body temperature so that it remains in place on the skin and does not spread or run of f after application. The gel-like consistency, which is due to the viscoelastic properties of polymer solutions in solvents, depends upon molecular weight, degree of substitution as well as, for derivatives such as EHEC where the several units of derivatising agent may be added to each derivatised saccharide hydroxyl group, the molar substitution and type of substituent as well as the concentrations of polymer in the composition. The compositions should generally have high viscosity under low shear but, for optimal handling during manufacture and application, should be shear thinning. This combination of features can be achieved by appropriate selection of properties, as illustrated in the accompanying examples, for instance. For example, the viscosity-increasing effect of EHEC depends on the degree of polymerization and on the degree of substitution and, for the EHEC having a degree of polymerisation of 3200, mentioned above, a suitable concentration in ethanol is 0.5 to 2.0%, for instance around 1.0%.

This, for example, applies to pH-regulating agents such as bases, eg alkaline inorganic compounds or organic bases and mixtures by which the action of the alcohol is increased under certain circumstances. Inorganic bases which may be used include sodium and potassium hydroxide and carbamate. Organic bases include triethylamine, triethanol amine and other alkanolamines. For example, a content of 0.02% NaOH will increase the antiviral action of the ethanol. Thus in one embodiment of the invention the composition has a pH in the range 6 to 9.5, preferably an alkaline pH. Other additives that can be mentioned are the substances that form part of medicinal gels such as emollients, colorants, perfumes, menthol, camphor, W-protective agents etc. and the like by which the gel can be supplemented with further functional properties.

The composition should, however, be substantially free of pharmacologically active ingredients other than these optional enhancing agents.

The composition is preferably supplied in an air and moisture/moisture vapour-impermeable container. Such containers are, for instance, squeezable tubes, especially formed of metal foils or of plastics materials having moisture barrier properties. Such containers prevent compositions, whose water content is such that the composition is hygroscopic, from absorbing moisture from the atmosphere during storage and before use. By the use of such containers, therefore loss of drying activity of the gels is minimised.

According to the invention we have not only succeeded in producing a gel—with a concentrated content of alkanol—which is very effective and suitable for treatment of skin diseases, which is skin-adhesive and gentle to the skin, and which preferably does not contain other medicaments or pharmaceuticals. The mere omission of medicaments and pharmaceuticals such as antihistamines etc. has as a consequence that no reverse actions or side-effects occur and that allergic reactions are completely eliminated. Further to this, as a consequence of the special mechanism of activity of ethanol, absolutely no resistance can develop among the responsible microorganisms or parasites. In choosing a gel with a matrix structure it is achieved that the ethanol, after application, does not accumulate in, for example, the nasolabial fissure at the angle of the mouth or in the groin but remains where applied. Further, as the gel shows pseudoplastic (viscoelastic) properties the gel is very easy to apply, and at the same time it regains its matrix structure and its structural firmness and exactly by that, as mentioned, remains on the site of application.

Because of the high concentration of alcohol the gel possesses other surprising properties. The skin-adhesive properties turn out to be very good, partially due to, the high content of alkanol, but also because of the choice of gelling agent, where especially EHEC, ASP, and PVP or combinations of these have lipophilic and hydrophilic properties giving the alcohol a very good contact with the skin.

The gelling agents, especially EHEC, ASP, and PVP or combinations of these, have hydrophobic-hydrophilic properties by which the release of alcohol towards the skin from the slow release matrix structure of the gel is adjustable. By doing this, it can be obtained that no release-inhibiting film is created between the alcohol-gel and the skin/mucous membranes. This, of course, is important for the continuous effect of the alcohol-gel on the site of application.

Thus, it is not necessary to add surfactants to achieve the correct contact between the skin and the gel as is the case in U.S. Pat. No. 4,593,048. The composition should generally be free of added surfactants.

Similarly, it is not necessary to add special binding agents nor to use plaster or tape in order to adhere the gel to the skin.

Gels according to the invention are physically and chemically stable for at least 12 months at 50° C. Among other things this is a result of the fact that addition of other active ingredients or adjuvants, which together with medicament or biocide may be labile during production and storage, is not needed. It is not necessary to add actual medicaments that, in turn, would require protective antioxidants etc. to secure the chemical stability of the very same medicaments during production and storage.

As the gel does not contain actual skin irritants it is, as mentioned, not necessary to add anti-irritants such as antihistamines, anti-inflammatory agents or similar agents.

Because of the concentrated content of alcohol the gel is self-preserving. It is therefore not necessary to add antimicrobial preservatives against fungoid growths nor products against bacteria or other micro-organisms, and it is not necessary to store the gel in refrigerator or the like. Omitting all these additives in the gel means that undesirable side-effects of such additives are eliminated.

Two very important properties are achieved in the invention by omitting surfactants, skin adhesives, pharmaceuticals, medicaments, antioxidants, antihistamines, or other anti-inflammatory agents, and because it is not necessary to add preservatives against fungi, bacteria, or other micro-organisms to the gel. First, in all simplicity, the gel is composed of non-allergenic substances. Secondly, owing to its special mode of action towards the infectious agents ethanol does not give rise to development of resistance. Furthermore the product does not disturb the hosts immune response.

For the sake of completeness it should be mentioned that many skin diseases, for example, Herpes simplex are complicated by secondary, usually bacterial infections. It is not necessary to add other pharmaceuticals to the gel to avoid secondary infections, as the alcohol in the gel with the long-term effect disinfects the area and protects it against reinfection via the plaster effect of the dried gel until the wound has healed.

Especially regarding Herpes infections the drying and protein coagulating effect is of great importance. During the primary phase of the repeated herpes outbreaks (secondary infections) are characterized by the formation of blisters, full of liquid. Apart from an immediate improvement of the itching and the pain reaction, a drying action on the blisters, that have already formed, is achieved when the preparation is applied at an early stage, and thus the blisters will disappear rapidly. If the herpes outbreak is not treated early enough the blisters will burst resulting in the formation of suppurating, open wounds that are characteristic of the secondary phase. When used during this phase, the preparation has an immediate drying effect by means of which the secretion ends, and the protein coagulating action destroy the superficial, necrotic cells. The drying effect makes the product useful on moist skin areas. Here the drying effect has an immediate prophylactic action in relation to bacterial infections through a reduction of the growth conditions.

Similar advantages are seen when the gel is used to treat skin eruptions associated with other viral infections such as chickenpox. When applied to such skin eruptions the formation of blisters is prevented or they are dried and itching is minimised. The breaking of the skin with subsequent risk of infection is thus prevented.

In this connection we can also mention accidental skin injuries such as wounds and skin abrasions where the antimicrobial effect combined with the plaster action of the gel after drying has an indisputable preventive action in relation to wound infections.

The gel is further suitable for prophylactic treatment of physical skin injuries such as cuts, abrasions etc. This indication is not only based on the antimicrobial property of the preparation, but also on the protective effect of the dried gel having the "built-in" plaster effect that is achieved when the preparation has dried.

It is believed that use of the preparation in connection with treatment of burns will have a useful infectious prophylactic effect. Some eczematous diseases including allergic skin diseases are characterized by secondary infections. Here the invention will have great importance too, not least because of the non-allergenic property of the composition.

As mentioned above the gel is suitable for controlling externally parasitical and troublesome organisms. For example, the gel is suitable for external treatment of scabies, chigger and other ectoparasites.

A very effective preparation against skin infections and for eliminating external skin parasites can be obtained when using a gel in which the liquid consists of concentrated ethanol or a concentrated mixture of ethanol and other short-chained alcohols such as isopropanol or propylene glycol and containing in addition, additives such as drying and disinfecting agents, as well as the gelling agent, but no other ingredients.

The gel is also found to be useful for application to the site of inset bites and stings. The effect is thought to be due at least partially to the function of the concentrated alcohol in causing toxoid proteins in the sting to coagulate and be rendered inactive.

The invention is further illustrated in the following examples.

EXAMPLES

Examples of compositions of the gel:

Example 1

| Ingredient | Weight in % |
| --- | --- |
| Ethanol 99.9% | 91 |
| Water | 7 |
| Carbopol 980 NF | 2 |

Carbopol 980 NF (trade mark, BF Goodrich) has a molecular weight of around $7.5 \times 10^5$.

Example 2

| Ingredient | Weight in % |
| --- | --- |
| Ethanol 999% | 95 |
| Water | 3 |
| carbopol 980 NF | 2 |
| Perfume | — |

Example 3

| Ingredient | Weight in % |
| --- | --- |
| Ethanol 99.9% | min. 99 |
| Carbopol 940 NF* | max. |

*Carbopol 940 NF (registered trademark) an acrylic acid polymer from BF Goodrich

Example 4

| Ingredient | Weight in % |
| --- | --- |
| Ethanol 99.9% | 97.3 |
| Bermocoll OS* | 2.3 |
| NaOH or triethylamine | 0.1 |
| Water | 0.3 |

*Bermocoll OS (registered trademark) from Berol-Nobel = Ethyl (hydroxyethyl)cellulose

Example 5

| Ingredient | Weight in % |
| --- | --- |
| Ethanol 99.9% | 91.0 |
| EHEC* | 1.5 |
| Glycerine | 1.0 |
| Propyleneglycol | 3.0 |
| Water | 3.5 |

(DP = 1,600, DS-ethyl = 0.8, MS-hydroxyethyl = 2.0)

Example 6

| Ingredient | Weight in % |
| --- | --- |
| Ethanol 99.9% | 91.0 |
| PVP K-30* | 2.5 |
| UV-absorbent | 1.0 |
| Camphor | 0–0.5 |
| Propylene glycol or adjuvant | 0–3.0 |
| Water | 0–2.0 |
| Polyvinyl alcohol | 0–1.0 |

*PVP K-30 (registered trademark) from GAF = Polyvinylpyrrolidone, average molecular weight of $4 \times 10^4$.

Example 7

| Ingredient | Weight in % |
| --- | --- |
| Ethanol | 91 |
| Carbopol 940 | 1 |
| PVP K-90 | 2 |
| Water | 4 |
| Surfactant | 2 |

Example 8

| Ingredient | Weight in % |
| --- | --- |
| Ethanol | 91.0 |
| Hydroxypropylcellulose | 2.5 |
| Xanthan gum | 0.1 |
| Isopropanol | 4.0 |
| Water | 2.4 |

The hydroxypropyl cellulose is selected for its solubility in the liquid.

Example 9

| Ingredient | Weight in % |
| --- | --- |
| Ethanol | 93.0 |
| Hydroxyethylcellulose | 1.0 |
| Ethylcellulose | 0.5 |
| Methylcellulose | 0.5 |
| NaOH | 0.02 |
| Water | 4.98 |

All the cellulose derivatives are selected for their solubility in the liquid.

Example 10

| Ingredient | Weight in % |
| --- | --- |
| Ethanol | 95.0 |
| Ethylhydroxyethylcellulose (Bermocoll OS) | 1.0 |
| Polyvinylpyrrilidone (MW $3.5 \times 10^4$) | 2.2 |
| Polyethyleneglycol (MW $2 \times 10^3$) | 0.2 |
| KOH | 0.02 |
| Water | 1.58 |

Examples of the use of the gels:

Example 11
Local treatment of Herpes simplex

When used for local treatment of Herpes simplex the effect depends on the time of application in relation to the start of the infection. Gels with particularly high concentration of alcohol are suitable, for example, gels mentioned in example 3, 4 or 10.

Within the first hours of the first phase which is characterized by itching, slight pain and prickling, followed by formation of vesicles, the gel is applied to the affected area approximately once an hour. The subjective symptoms dwindle immediately, and after 3–5 applications the outbreak is stopped and the vesicles disappear. After this, the gel is re-applied every 3–5 hours for 24 hours to secure that the outbreak has stopped completely.

When treatment is not started before the vesicles have burst and the gel is applied with a frequency of about every 3 hours the wounds are kept dry without the suppuration. The treatment is continued with decreasing application frequency until all wounds have started healing.

All three gels gave good results when used at these stages of the infection.

Example 12
Treatment of Herpes zoster

When used for treating local skin outbreaks of Herpes zoster the gel mentioned in example 2 and 9 have been applied to the affected area. During the first 24 hours the gel is applied approximately every 2 hours, and after that at longer intervals as required. The vesicles heal up and the patient's inconveniences will abate rapidly.

Example 13
Treatment of bacterial skin infections

The treatment of skin infections in connection with Acne vulgaris should be mentioned as an example of treating bacterial skin infections.

Gel in accordance with examples 1 and 6 according to the invention is applied to the infected skin areas. To begin with the gel is applied 3 times a day, and after that, when the infected areas have dried it is applied approximately once or twice a day. By means of this treatment with each of the gels rapid healing is achieved. A gel, in accordance with example 3, can be used in difficult cases directly on extensively infected areas.

Example 14
Treatment of mycologic skin infections

The treatment of epidermophytosis (*Tinea pedis*) should be mentioned as an example of treating mycologically conditioned infections. Rapid healing of fissures, and successive cure of the fungus infection is achieved when a gel, in accordance with example 4, 7 and 8, is applied twice a day primarily, and after a few days only once a day.

Example 15
Control of external parasites

As required a thin or thick layer of a gel, in accordance with example 3 and 9 of the invention, is applied to the infected area with the external parasites such as lice, scab mites, ticks and crab lice. In a short time the parasites are eliminated.

Because of the antimicrobial property of the gel, secondary infections after bites also heal up rapidly.

Example 16
Prophylacticum against skin infections

The treatment of banal scraping wounds should be mentioned as an example of using the gel as a prophylacticum. Primarily the wound is cleansed with water/soap following classic principles. After that, gel is applied, for example, the gel mentioned in example 1. During the first 24 hours the gel is applied 3 times. After that, the gel is applied once a day until the wounds start to heal. Due to the properties of the dried gel, acting as an elastic, fixed plaster on the wound, a good protection of the wounds is achieved in between the applications.

Example 17
Treatment of Chicken pox (Variola)

The gel of example 4 is applied directly onto the individual eruptions on the skin of a patient with chickenpox as soon as possible after the eruption and every 2 to 4 hours thereafter. This immediately soothes the skin, reduces itching, prevents blister formation and renders the patient non-contagious in a shorter period of time. The gels of examples 3 and 10 have similar activity.

Example 18
Bee Sting and Other Insect Bite Treatment

The gel of example 4 is applied direct to the skin at the site of a bee sting as soon as possible after occurrence of the sting. The discomfort and swelling were immediately reduced and itching does not develop. This activity is thought to be due to an effect of the concentrated alcohol in coagulating protein in the insect venom injected into the skin. The gels of examples 3 and have similar performance.

We claim:

1. A gel form pharmaceutical composition for the treatment of skin disorders comprising a liquid and a polymer gelling agent dissolved in the liquid, wherein the composition comprises more than 90% by weight of at least one $C_{1-4}$ alkanol based on the total weight of the composition and less than 10% by weight water based on the total weight of the composition, wherein said polymer gelling agent has a molecular weight of at least 10,000, wherein said alkanol is substantially the only active agent in said composition and said composition is free of any additional ingredients which would substantially reduce gel stability.

2. A composition according to claim 1 in which the concentration of water in the composition is less than the equilibrium content at temperatures in the range 20–24° C. and 50 to 100% relative humidity.

3. A composition according to claim 1 consisting essentially of the gelling agent, alkanol and water.

4. A composition according to claim 1, wherein said composition further consists essentially of an effective amount of an enhancing agent which enhances the effect of the alkanol in the treatment of said skin disorder.

5. A composition according to claim 4 wherein the enhancing agent consists of a base.

6. A composition according to claim 1 in which the alkanol is selected from ethanol, isopropanol or mixtures thereof.

7. A composition according to claim 1 in which the gelling agent is a derivative of cellulose.

8. A composition according to claim 1 in which the concentration of water is less than 5% based on the weight of alkanol plus water.

9. A composition according to claim 1 contained in a moisture- and moisture vapour-impervious container.

10. A method for the treatment of skin infected by a virus comprising administering a polymer gelling agent and more than 90% by weight of at least one $C_{1-4}$ alkanol and less than 10% water, based on the total composition weight to a patient in need of said treatment, wherein said alkanol is substantially the only active agent in said composition and said composition is free of any additional ingredients which would substantially reduce gel stability.

11. The method according to claim 10 in which the viral infection is of Herpes simplex virus.

12. A method for the treatment of skin having ectoparasites comprising applying to the skin of a patient in need of such treatment a composition comprising a polymer gelling agent and more than 90% by weight of at least one $C_{1-4}$ alkanol and less than 5% by weight of water, based on the total composition, wherein said alkanol is substantially the only active agent in said composition.

13. A method of treatment of infected skin by topical application to the infected area of skin of a gel form pharmaceutical composition comprising a polymer gelling agent, more than 90% by weight of at least one $C_{1-4}$ alkanol, based on the weight of the total composition and less than 10% by weight water based on the total weight of composition, wherein said alkanol is substantially the only active agent in said composition and said composition is free of any additional ingredients which would substantially reduce gel stability.

14. A method according to claim 13 in which the treatment is effective to affect a layer of skin deeper than the stratum corneum.

15. A method according to claim 13 in which the composition remains in contact with the area affected by the infection for a period of at least 2 hours, to form a cohesive barrier film of said polymer.

16. A method of treatment of disorders of layers of the skin below the stratum corneum by topical application to the skin of a composition as recited in claim 1.

17. A composition according to claim 5 wherein said base is an inorganic alkali.

18. A composition according to claim 17 wherein said inorganic alkali is sodium hydroxide or potassium hydroxide.

19. A composition according to claim 5 wherein said base is an organic base.

20. A composition according to claim 19 wherein said organic base is triethylamine.

21. A composition according to claim 6 in which the alkanol is ethanol.

22. A composition according to claim 7, in which the derivative of cellulose is a cellulose ether.

23. A composition according to claim 7 in which the derivative of cellulose is ethyl hydroxyethyl cellulose.

24. A composition according to claim 5, wherein the enhancing agent is added in an amount such that the composition has a pH in the range from 6 to 9.5.

25. A composition according to claim 18, wherein sodium hydroxide or potassium hydroxide is added in an amount such that the composition has a pH in the range from 6 to 9.5.

26. A composition according to claim 20, wherein triethylamine is added in an amount such that the composition has a pH in the range from 6 to 9.5.

27. A composition according to claim 1, consisting of gelling agent, liquid consisting of $C_{1-4}$ alkanol and water, and optional additives selected from the group consisting of pH regulating agents, emollients, colorants, perfumes, menthol, camphor, and UV protective agents.

28. A composition according to claim 1, which is substantially free of antihistamines, anesthetics and anti-inflammatories.

29. A composition according to claim 24, wherein the amount of water in the composition is below the equilibrium content of water in the composition at 20 to 37° C. and at 50 to 100% relative humidity.

30. A composition according to claim 1, wherein the alkanol is a $C_{3-4}$-alkanol.

31. A composition according to claim 1, wherein the alkanol is a $C_3$-alkanol.

32. A method according to claim 12, wherein said ectoparasites cause scabies.

* * * * *

UNITED STATES PATENT AND TRADEMARK OFFICE
CERTIFICATE OF CORRECTION

PATENT NO. : 5,981,605
DATED : Nov. 9, 1999
INVENTOR(S) : Thomsen et al.

It is certified that error appears in the above-identified patent and that said Letters Patent is hereby corrected as shown below:

Please amend the claims at columns 12-14 as follows.

1. A gel form pharmaceutical composition for the treatment of skin disorders comprising a liquid and a polymer gelling agent dissolved in the liquid, wherein the composition comprises more than 90% by weight of at least one $C_{1-4}$ alkanol based on the total weight of the composition and less than 10% by weight water based on the total weight of the composition, wherein said polymer gelling agent has a molecular weight of at least 10,000, wherein <u>the active agent consists essentially of</u> said alkanol [is substantially the only active ingredient in said composition] and said composition is free of any additional ingredients which would substantially reduce gel stability<u>, irritate the skin, act as an allergen, or lead to the development of resistance</u>.

UNITED STATES PATENT AND TRADEMARK OFFICE
CERTIFICATE OF CORRECTION

PATENT NO. : 5,981,605
DATED : Nov. 9, 1999
INVENTOR(S) : Thomsen et al.

It is certified that error appears in the above-identified patent and that said Letters Patent is hereby corrected as shown below:

10. A method for the treatment of skin infection by a virus comprising administering a polymer gelling agent and more than 90% by weight of at least one $C_{1-4}$ alkanol and less than 10% water, based on the total composition weight to a patient in need of said treatment, wherein the active agent consists essentially of said alkanol [is substantially the only active ingredient in said composition] and said composition is free of any additional ingredients which would substantially reduce gel stability, irritate the skin, act as an allergen, or lead to the development of resistance.

UNITED STATES PATENT AND TRADEMARK OFFICE
CERTIFICATE OF CORRECTION

PATENT NO. : 5,981,605
DATED : Nov. 9, 1999
INVENTOR(S) : Thomsen et al.

It is certified that error appears in the above-identified patent and that said Letters Patent is hereby corrected as shown below:

17. A method of treatment of infected skin by topical application to the infected area of skin of a gel form pharmaceutical composition comprising a polymer gelling agent, more than 90% by weight of at least one $C_{1-4}$ alkanol, based on the weight of the total composition and less than 10% by weight water based on the total weight of the composition, wherein <u>the active agent consists essentially of</u> said alkanol [is substantially the only active ingredient in said composition] and said composition is free of any additional ingredients which would substantially reduce gel stability<u>, irritate the skin, act as an allergen, or lead to the development of resistance</u>.

Signed and Sealed this

Twenty-seventh Day of March, 2001

Attest:

NICHOLAS P. GODICI

Attesting Officer

Acting Director of the United States Patent and Trademark Office